(12) United States Patent
Hoem et al.

(10) Patent No.: US 10,952,883 B2
(45) Date of Patent: Mar. 23, 2021

(54) COMBINED STENT REPERFUSION SYSTEM

(71) Applicant: CorFlow Therapeutics AG, Baar (CH)

(72) Inventors: Jon H. Hoem, Oberageri (CH); Robert S. Schwartz, Inver Grove Heights, MN (US); Martin T. Rothman, Santa Rosa, CA (US)

(73) Assignee: CorFlow Therapeutics AG, Baar (CH)

( * ) Notice: Subject to any disclaimer, the term of this patent is extended or adjusted under 35 U.S.C. 154(b) by 155 days.

(21) Appl. No.: 15/926,911

(22) Filed: Mar. 20, 2018

(65) Prior Publication Data

US 2018/0280172 A1 Oct. 4, 2018

Related U.S. Application Data

(60) Provisional application No. 62/473,740, filed on Mar. 20, 2017.

(51) Int. Cl.
*A61F 2/958* (2013.01)
*A61B 17/12* (2006.01)
(Continued)

(52) U.S. Cl.
CPC .......... *A61F 2/958* (2013.01); *A61M 25/0032* (2013.01); *A61M 25/104* (2013.01);
(Continued)

(58) Field of Classification Search
CPC .............. A61F 2/958; A61F 2002/9583; A61F 2250/0067; A61F 2/013; A61M 25/1011; A61M 2025/0183; A61M 2025/1052; A61M 25/104; A61M 2025/0057; A61M 2025/1013; A61M 2025/1015; A61M 2025/105; A61M 2025/1079; A61M 1/0088; A61M 2005/14506; A61M 2025/0002; A61M 2025/0004;
(Continued)

(56) References Cited

U.S. PATENT DOCUMENTS

| 6,156,005 A | 12/2000 | Theron |
| 7,837,650 B1 * | 11/2010 | Cox ..................... A61M 25/104 604/110 |

(Continued)

FOREIGN PATENT DOCUMENTS

| WO | WO 01/70325 A2 | 9/2001 |
| WO | WO2017/120229 A1 | 7/2017 |

OTHER PUBLICATIONS

WIPO, U.S. International Search Authority, International Search Report and Written Opinion dated May 25, 2018 in International Patent Application No. PCT/US2018/023422, 9 pages.

(Continued)

*Primary Examiner* — Eric J Rosen
*Assistant Examiner* — Mikail A Mannan
(74) *Attorney, Agent, or Firm* — Eversheds Sutherland (US) LLP; Christopher C. Bolten; Nicola A. Pisano

(57) ABSTRACT

Devices and methods for preventing reperfusion injuries when an occlusion balloon is deflated. A catheter having an infusion lumen exiting the catheter distal of a stent balloon and/or occlusion balloon allows a therapeutic agent to be introduced to a target location to establish desired temperatures and pressures prior to deflation of the balloon such that negative effects of reperfusion are minimized.

9 Claims, 2 Drawing Sheets

(51) Int. Cl.
*A61M 25/10* (2013.01)
*A61M 25/00* (2006.01)
*A61B 17/00* (2006.01)
*A61B 90/00* (2016.01)

(52) U.S. Cl.
CPC ...... *A61M 25/1011* (2013.01); *A61B 17/1204* (2013.01); *A61B 17/12109* (2013.01); *A61B 17/12136* (2013.01); *A61B 2017/00084* (2013.01); *A61B 2017/00243* (2013.01); *A61B 2090/064* (2016.02); *A61M 2025/0037* (2013.01); *A61M 2025/105* (2013.01); *A61M 2025/1061* (2013.01)

(58) Field of Classification Search
CPC .. A61M 2025/0006; A61M 2025/0073; A61M 2025/0079; A61M 2025/1093; A61M 2025/1095; A61M 2025/1097; A61M 2205/3306; A61M 2205/3337; A61M 2205/3344; A61M 2230/50; A61M 25/0043; A61M 25/04; A61M 25/09; A61M 25/0905; A61M 25/10; A61M 25/1018; A61M 25/10182; A61M 25/10185; A61M 25/10188; A61M 39/24; A61M 5/007; A61M 5/142; A61M 5/1452; A61M 5/1723; A61M 2025/0037; A61M 25/105; A61M 25/1061; A61M 25/0032; A61M 2025/1061; A61B 17/1204; A61B 17/12109; A61B 17/12136; A61B 2017/00084; A61B 2017/00243; A61B 2090/064

See application file for complete search history.

(56) References Cited

U.S. PATENT DOCUMENTS

| | | |
|---|---|---|
| 2005/0267561 A1 | 12/2005 | Jones et al. |
| 2008/0300573 A1 | 12/2008 | Consigny et al. |
| 2010/0280451 A1 | 11/2010 | Teeslink et al. |
| 2011/0196255 A1 | 8/2011 | Kassab |
| 2012/0265079 A1* | 10/2012 | Hilmersson .......... A61B 5/0215 600/483 |
| 2012/0265283 A1 | 10/2012 | Mack et al. |
| 2013/0165858 A1 | 6/2013 | Cox et al. |
| 2017/0189654 A1 | 7/2017 | Schwartz et al. |

OTHER PUBLICATIONS

European Patent Office, Supplementary European Search Report dated Apr. 24, 2020 in European Patent Application No. 18771178, 9pp.

\* cited by examiner

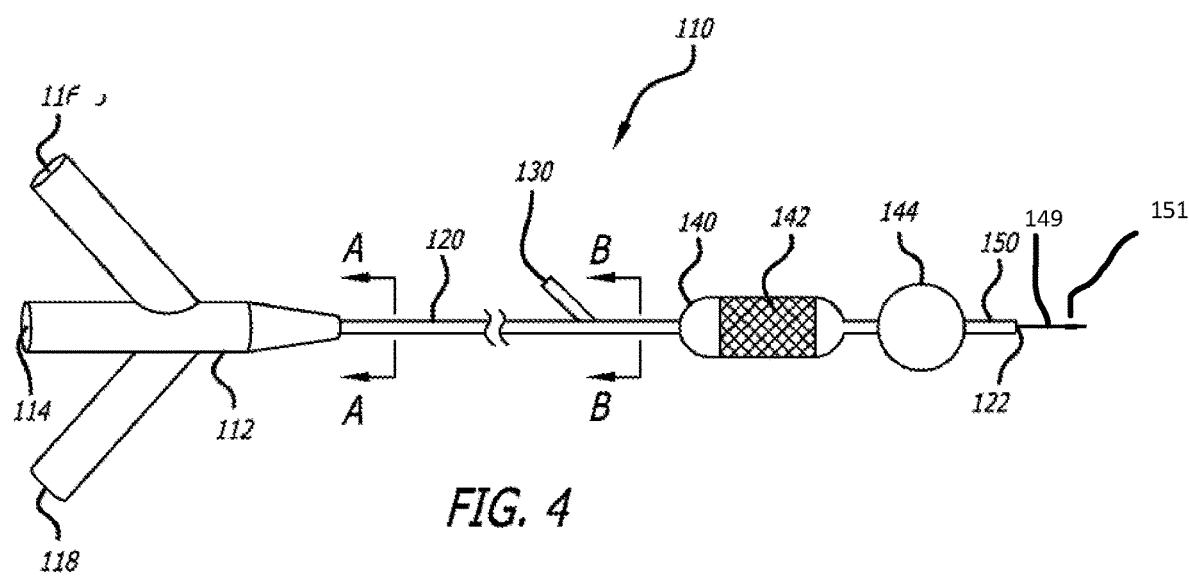
FIG. 4
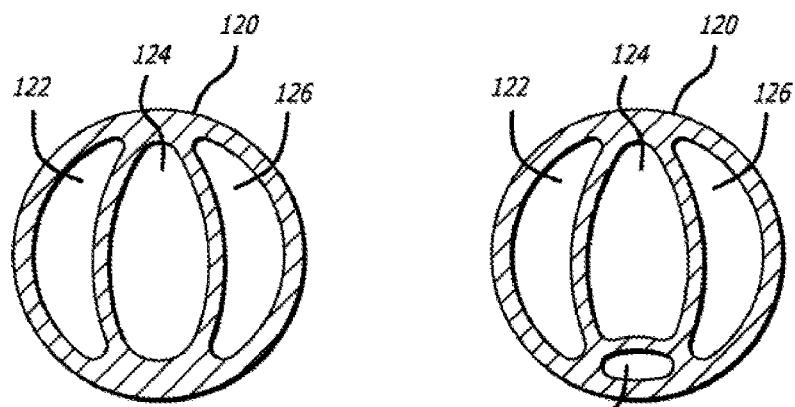
FIG. 5
FIG. 6

COMBINED STENT REPERFUSION SYSTEM

RELATED APPLICATIONS

This application claims priority to Provisional Patent Application Ser. No. 62/473,740, filed Mar. 20, 2017, entitled Combined Stent Reperfusion System, which is hereby incorporated herein by reference in its entirety.

BACKGROUND OF THE INVENTION

The coronary microcirculation is critical for normal cardiac function, and myocardial infarction (MI) with subsequent ischemic cardiomyopathy are the most common causes of cardiac morbidity and mortality. Microvascular obstruction and no reflow are the principal causes of post-MI heart failure, adverse LV remodelling, scar/aneurysm formation and arrhythmias.

Recent publications by Hervas and Bulluck, incorporated by reference herein, have documented that the fundamental trigger for MVO is the reperfusion itself. I.e., it is the reopening of the coronary artery which triggers formation of MVO and MVO in itself is an independent predictor for patient outcomes in acute heart attack patients. Thus, there is a need for a method and device that targets the reduction of reperfusion injury, thus potentially reducing the formation of MVO.

Technologies have been recently developed to diagnose and treat MVO and are described in U.S. patent application Ser. No. 15/3984,470 and PCT Application Ser. No. PCT/US2017/012181, both to Schwartz et al. and entitled System and Method for Treating MVO. The entireties of these references are incorporated by reference herein. These references describe an easy-to-use, reliable technology that simultaneously measures and treats coronary MVO (STEW, NSTEMI UA, Stable Angina etc.) in the catheterization lab. The technology, if desired, can be used independently for coronary and microvascular diagnosis, separately for treatment if desired.

ASPECTS AND SUMMARY OF THE INVENTION

The present invention provides a technology that combines the delivery of a coronary stent with a system for treating microvascular obstructions while avoiding reperfusion injuries.

One aspect of the invention pertains to the placement of a stent using an occlusion and perfusion catheter to diagnose and treat microvascular obstruction/no reflow, and to avoid reperfusion injury. According to this aspect, a catheter is provided with a stent placed over a balloon delivery system and is used for revascularizing the heart and/or other organs including, but not limited to, the brain, lungs, kidneys, muscles, intestines etc.

The catheter may be placed over a pressure/temperature-sensing guidewire to allow for real-time measurement of distal vessel pressure and temperatures, i.e. distal to the balloon delivery system. Alternatively, the measurement technology may be mounted directly to the delivery catheter.

In one aspect, the catheter has an infusion lumen, which can infuse cardioprotective or therapeutic agents into the coronary circulation.

Another aspect of the invention is a system that can infuse cardio-protective and/or therapeutic agents into the microcirculation before a stent delivery balloon is collapsed. In this way the stent balloon, while inflated, acts as an occlusion balloon. Furthermore, the catheter lumen is available to deliver a cardio-protective agent to reduce the potential negative effect of the reintroduction of blood flow when the balloon is deflated. After deflation, the stent remains in place to promote continued epicardial perfusion of the coronary tree.

Yet another aspect of the invention provides a stent delivery balloon with an occlusion balloon. These two balloons may have different properties.

In one embodiment the stent delivery balloon and the occlusion balloon may be mounted on a catheter shaft. They may be fixed longitudinally to the shaft or may be mounted such that the longitudinal position is adjustable to offer more accurate placement.

Another aspect of the invention is a method of reperfusing using a catheter having a stent delivery balloon and an occlusion balloon. The method begins by placing a catheter into the artery, preferably over a rapid exchange wire with pressure and temperature-sensing capabilities at a distal end of the guide wire. The occlusion balloon is then inflated to avoid reperfusion. The stent is then delivered by inflating the stent delivery balloon. Once the stent is in place, the stent delivery balloon is deflated. The occlusion balloon remains inflated to prevent reperfusion from occurring. A cardio-protective agent is then infused through the infusion lumen of the catheter. During this time, the effect of the cardio-protective agent is measured with the pressure/temperature sensor. Once the cardio-protective effect is achieved, the occlusion balloon is deflated. After the blood reperfuses, the degree of microvascular damage can be measured and potentially treated.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 4 is a perspective view of an embodiment of a single balloon inflation system of the invention;

FIG. 5 is a section view taken along lines A-A of FIG. 1; and,

FIG. 6 is a section view taken along lines B-B of FIG. 1.

DESCRIPTION OF EMBODIMENTS

Figure 1:
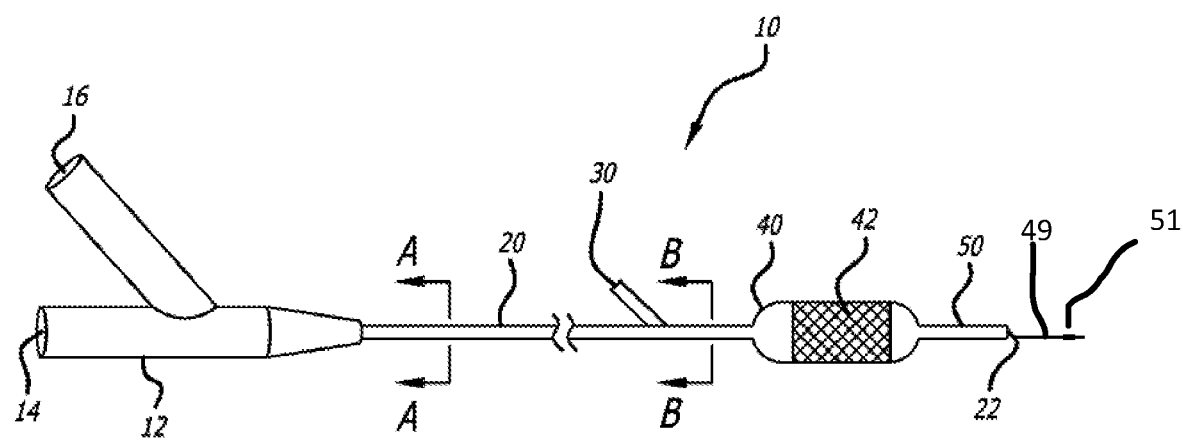
FIG. 1 is a perspective view of an embodiment of a single balloon inflation system of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

FIG. 1 shows a single balloon embodiment 10 of a delivery system of the invention. The delivery system 10 includes a manifold 12 at a proximal end that includes an infusion port 14 and a stent balloon inflation port 16. The manifold tapers to a flexible catheter 20 that proximally contains two lumens—an infusion lumen 22 that is in fluid communication with the infusion port 14 and an inflation lumen 24 that is in fluid communication with the balloon inflation port 16.

Figure 2:
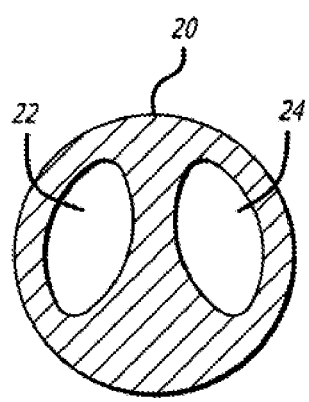
FIG. 2 is a section view taken along lines A-A of FIG. 1.

FIG. 2 is a cross section of the catheter 20 taken along section lines A-A of FIG. 1. FIG. 2 shows the infusion lumen 22 and the inflation lumen 24.

Figure 3:
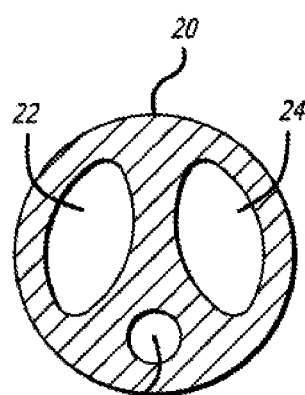
FIG. 3 is a section view taken along lines B-B of FIG. 1.

Proceeding distally in FIG. 1, there is shown a therapeutic agent or Rx port 30 that leads to an Rx lumen 32 in the catheter 20. FIG. 3 shows a cross section of the catheter 20 taken along section lines B-B of FIG. 1. It can thus be seen that distal of the Rx port, the catheter has three lumens, an infusion lumen 22, an inflation lumen 24 and an Rx lumen 32.

Distal of the Rx port 30 is a balloon 40 with a stent 42. The balloon 40 is in fluid communication with the inflation lumen 24 such that fluid passing distally through the inflation lumen 24 terminates in the balloon 40.

A stent 42 surrounds the balloon 40 and is expanded thereby when the balloon 40 in inflated. The stent 42, due to its memory properties, remains expanded after the balloon 40 deflates. Thus, deflating balloon 40 results in separation of the stent 42.

Distal of the balloon 40 is the distal end 50 of the catheter 20. The distal end 50 includes an open end of the infusion lumen 22.

In use, the delivery device 10 involves routing the catheter 20 over a guide wire 49 to the target site. The infusion lumen 22 is used as a guidewire lumen while the device 10 is being advanced to the target site. The guidewire preferably includes a pressure and temperature sensor 51 to provide real-time measurement of distal vessel pressures and temperatures at a location distal of the balloon delivery system.

Once the device 10 has reached its target location, the balloon 40 is inflated causing the stent 42 to expand against the native tissue. The inflation of the balloon 40 also results in an occlusion of the vessel.

While the balloon 40 remains inflated and the vessel occluded, a cardio-protective agent is infused via the infusion port 30 and through the infusion lumen 32, exiting the lumen 32 at the distal end 50 of the catheter, downstream of the occlusion balloon 40. The cardio-protective agent reduces the potential negative effects of reintroducing blood flow when the balloon 40 is deflated.

Once the desired cardio-protective effect has been achieved, as measured by the pressure/temperature sensor on the guidewire, the balloon 40 is deflated, allowing normal blood reperfusion of the coronary circulation. The stent 42 remains in place and secures continued epicardial perfusion of the coronary tree. After blood reperfusion is complete, the degree of microvascular damage can be measured and potentially treated as described in the incorporated references.

FIG. 4 shows a dual balloon embodiment 110 of a delivery system of the invention. The delivery system 110 includes a manifold 112 at a proximal end that includes an infusion port 114, a stent balloon inflation port 116, and an occlusion balloon inflation port 118. The manifold tapers to a flexible catheter 120 that proximally contains three lumens—an infusion lumen 122 that is in fluid communication with the infusion port 114, a stent balloon inflation lumen 124 that is in fluid communication with the stent balloon inflation port 116, and an occlusion balloon inflation lumen 126 that is in fluid communication with the occlusion balloon inflation port 118.

FIG. 5 is a cross section of the catheter 120 taken along section lines A-A of FIG. 4. FIG. 5 shows the infusion lumen 122 and the inflation lumen 124.

Proceeding distally in FIG. 6, there is shown a therapeutic agent or Rx port 130 that leads to an Rx lumen 132 in the catheter 20. FIG. 6 shows a cross section of the catheter 20 taken along section lines B-B of FIG. 4. It can thus be seen that distal of the Rx port, the catheter has four lumens, the infusion lumen 122, the inflation lumen 124, the occlusion lumen 126, and an Rx lumen 132.

Distal of the Rx port 130 is a balloon 140 with a stent 142. The balloon 140 is in fluid communication with the inflation lumen 124 such that fluid passing distally through the inflation lumen 124 terminates in the balloon 140.

A stent 142 surrounds the balloon 140 and is expanded thereby when the balloon 140 in inflated. The stent 142, due to its memory properties, remains expanded after the balloon 140 deflates. Thus, deflating balloon 140 results in separation of the stent 142.

Distal of the balloon 140 is an occlusion balloon 144. The occlusion balloon 144 is in fluid communication with the occlusion lumen 126 such that fluid passing distally through the occlusion lumen 126 terminates in the balloon 144.

Distal of the balloon 144 is the distal end 150 of the catheter 120. The distal end 150 includes an open end of the infusion lumen 122.

In use, the delivery device 110 involves routing the catheter 120 over a guide wire 149 to the target site. The infusion lumen 122 is used as a guidewire lumen while the device 110 is being advanced to the target site. The guidewire preferably includes a pressure and temperature sensor 151 to provide real-time measurement of distal vessel pressures and temperatures at a location distal of the balloon delivery system.

Once the device 110 has reached its target location, the occlusion balloon 144 is inflated to occlude the vessel and prevent reperfusion.

Next the stent balloon 140 is inflated causing the stent 142 to expand against the native tissue. The stent balloon 140 is then deflated, separating the stent 142 from the device.

While the occlusion balloon 144 remains inflated and the vessel occluded, a cardio-protective agent is infused via the infusion port 130 and through the infusion lumen 132, exiting the lumen 132 at the distal end 150 of the catheter, downstream of the occlusion balloon 144. The cardio-protective agent reduces the potential negative effects of reintroducing blood flow when the balloon 144 is deflated.

Once the desired cardio-protective effect has been achieved, as measured by the pressure/temperature sensor on the guidewire, the occlusion balloon 144 is deflated, allowing normal blood reperfusion of the coronary circulation. The stent 142 remains in place and secures continued epicardial perfusion of the coronary tree. After blood reperfusion is complete, the degree of microvascular damage can be measured and potentially treated as described in the incorporated references.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of delivery a stent while preventing injury due to reperfusion comprising:
   navigating a catheter including a stent to a target location within a vessel;
   monitoring a pressure and temperature of the target location;
   inflating a balloon disposed within the stent, thereby expanding the stent against a vessel wall of the target location and occluding the vessel;
   infusing an infusate into the vessel downstream of the balloon;
   analysing the pressure and the temperature to determine monitoring an effect of the infusion of the infusate;
   deflating the balloon once a desired effect of the infusion of the infusate has been reached based on the analysis.

2. The method of claim 1 wherein navigating the catheter comprises navigating a guidewire to the target location and then advancing the catheter over the guidewire.

3. The method of claim 1 wherein navigating the guidewire comprises navigating the guidewire having pressure and temperature sensors near a distal end thereof.

4. The method of claim 1 wherein monitoring an effect of the infusion of the infusate comprises monitoring a temperature and pressure at said target location distal of said balloon.

5. The method of claim 1 wherein said infusate comprises a cardio-protective agent.

6. A method of delivery a stent while preventing injury due to reperfusion comprising:
   navigating a catheter including a stent to a target location within a vessel;
   monitoring a pressure and temperature of the target location;
   inflating an occlusion balloon, thereby stopping blood flow through the vessel;
   inflating a stent balloon disposed within the stent, thereby expanding the stent against a vessel wall of the target location;
   deflating the stent balloon;
   infusing a cardio-protective agent into the vessel downstream of the balloon;
   analysing the pressure and the temperature to determine monitoring an effect of the infusion of the cardio-protective agent;
   deflating the occlusion balloon once a desired effect of the infusion of the cardio-protective agent has been reached based on the analysis.

7. The method of claim 5 wherein navigating the catheter comprises navigating a guidewire to the target location and then advancing the catheter over the guidewire.

8. The method of claim 6 wherein navigating the guidewire comprises navigating the guidewire having pressure and temperature sensors near a distal end thereof.

9. The method of claim 5 wherein monitoring an effect of the infusion of the cardio-protective agent comprises monitoring a temperature and pressure at said target location distal of said balloon.

\* \* \* \* \*